United States Patent
Joshi et al.

(10) Patent No.: US 8,138,381 B2
(45) Date of Patent: Mar. 20, 2012

(54) METHOD FOR RECOVERING A NATURAL GAS CONTAMINATED WITH HIGH LEVELS OF $CO_2$

(75) Inventors: Mahendra Ladharam Joshi, Katy, TX (US); Jingyu Cui, Katy, TX (US); Frederik Arnold Buhrman, Katy, TX (US); Scott Lee Wellington, Bellaire, TX (US); Stanley Nemec Milam, Houston, TX (US); Rogier Maarten Kamerbeek, Bellaire, TX (US)

(73) Assignee: Shell Oil Company, Houston, TX (US)

( * ) Notice: Subject to any disclaimer, the term of this patent is extended or adjusted under 35 U.S.C. 154(b) by 188 days.

(21) Appl. No.: 12/652,596

(22) Filed: Jan. 5, 2010

(65) Prior Publication Data

US 2010/0280288 A1    Nov. 4, 2010

Related U.S. Application Data

(60) Provisional application No. 61/142,971, filed on Jan. 7, 2009.

(51) Int. Cl.
*C07C 29/132* (2006.01)
*C07C 29/136* (2006.01)

(52) U.S. Cl. .............. 568/910; 568/865; 568/910.5; 518/700; 518/701; 518/702; 518/703; 518/704; 518/705

(58) Field of Classification Search .................. 568/885, 568/910, 910.5; 518/700–705
See application file for complete search history.

(56) References Cited

U.S. PATENT DOCUMENTS 3,841,058 A    10/1974    Templeman .................. 55/33

FOREIGN PATENT DOCUMENTS

| WO | WO0151412 | 7/2001 |
|---|---|---|
| WO | WO2009140317 | 11/2009 |

*Primary Examiner* — Elvis O Price

(57) ABSTRACT

The present invention provides a method for recovering a natural gas contaminated with high levels of carbon dioxide. A gas containing methane and carbon dioxide is extracted from a reservoir containing natural gas, where carbon dioxide comprises greater than 40 vol. % of the extracted gas. The extracted gas is scrubbed with a wash effective to produce a washed extracted gas containing less carbon dioxide than the extracted gas and at least 20 vol. % carbon dioxide. The washed extracted gas is oxidized with an oxygen containing gas in the presence of a partial oxidation catalyst to produce an oxidation product gas containing hydrogen, carbon monoxide, and carbon dioxide. The oxidation product gas is then utilized to produce a liquid methanol product.

17 Claims, 2 Drawing Sheets

METHOD FOR RECOVERING A NATURAL GAS CONTAMINATED WITH HIGH LEVELS OF $CO_2$

This application claims the benefit of U.S. Provisional Application No. 61/142,971 filed Jan. 7, 2009, which is incorporated herein by reference.

FIELD OF THE INVENTION

The present invention is directed to a method for recovering a natural gas contaminated with high levels of $CO_2$.

BACKGROUND OF THE INVENTION

Natural gas is a fuel gas used extensively in the petrochemical and other chemicals businesses. Natural gas is comprised of light hydrocarbons—primarily methane, with smaller amounts of other heavier hydrocarbon gases such as ethane, propane, and butane. Natural gas may also contain some quantities of non-hydrocarbon "contaminant" components such as carbon dioxide and hydrogen sulfide.

Natural gas is often extracted from natural gas fields that are remote or located off-shore. Conversion of natural gas to a liquid hydrocarbon is often required to produce an economically viable product when the natural gas field from which the natural gas is produced is remotely located with no access to a gas pipeline. One method commonly used to convert natural gas to a liquid hydrocarbon is to cryogenically cool the natural gas to condense the hydrocarbons into a liquid. Another method that may be used to convert natural gas to a liquid hydrocarbon is to convert the natural gas to a synthesis gas by partial oxidation or steam reforming, and subsequently converting the synthesis gas to methanol. Synthesis gas prepared from natural gas may also be converted to a liquid hydrocarbon by a Fisher-Tropsch reaction.

Non-hydrocarbon components of natural gas are generally considered contaminants when converting the natural gas to a liquid hydrocarbon. Carbon dioxide is one such non-hydrocarbon contaminant, particularly when present in the natural gas in large quantities.

In a cryogenic cooling process to liquefy hydrocarbons in a natural gas, carbon dioxide may crystallize when cryogenically cooling the natural gas, blocking valves and pipes used in the cooling process. Further, carbon dioxide utilizes volume in a cryogenically cooled liquid hydrocarbon/carbon dioxide mixture that would preferably be utilized only by the liquid hydrocarbon, particularly when the liquid hydrocarbon is to be transported from a remote location.

Carbon dioxide also may impair conversion of natural gas to synthesis gas so that a liquid hydrocarbon cannot be prepared by converting the natural gas to a synthesis gas and subsequently converting the synthesis gas to a liquid hydrocarbon (e.g. methanol). Significant quantities of carbon dioxide may impair conversion of a natural gas to synthesis gas by either partial oxidation or by steam reforming.

Partial oxidation of the natural gas to produce synthesis gas is usually effected by combustion of the natural gas with an oxygen containing gas at high temperatures—typically at least 700° C. when the partial oxidation is catalytically induced and at least 900° C. when the partial oxidation is effected with no catalyst. If a significant amount of carbon dioxide is present in the natural gas, the carbon dioxide tends to quench the combustion, limiting the effectiveness of the partial oxidation reaction to produce synthesis gas from the natural gas. Additionally, further processing a hot synthesis gas product produced by partial oxidation involves significant heat transfer and loss of thermal energy since the synthesis gas produced by partial oxidation must be cooled by at least 400° C., typically at least 500° C. to 700° C., prior to its utilization to produce a liquid hydrocarbon (e.g. methanol), and much thermal energy is lost in such heat transfers. Thermal energy loss from partial oxidation of a natural gas containing large quantities of carbon dioxide at temperatures exceeding 700° C. is particularly excessive since the large volume of carbon dioxide present in the natural gas must be extensively cooled after partial oxidation as well as the synthesis gas product.

Highly active partial oxidation catalysts, e.g. those disclosed in Applied Catalysis A: General, Volume 292, 18 Sep. 2005, pp. 177-188 consisting of rhodium or ruthenium on a carrier, may be used to effect a catalytic partial oxidation of methane or natural gas at lower temperatures, for example, from 350° C. to 700° C. Catalytic partial oxidation at these lower temperatures with these catalysts is disclosed to generate carbon dioxide as a product, which is undesirable when the starting feed material is already highly contaminated with carbon dioxide. Further, auto-ignition of a hydrocarboneous feed and an oxygen containing gas would be expected to be quenched by high levels of carbon dioxide at such low temperatures.

Steam reforming natural gas to produce synthesis gas is an endothermic process, unlike partial oxidation, and requires input of heat to drive the reaction. If a significant amount of carbon dioxide is present in the natural gas, the heat duty required to produce the synthesis gas is large since heat must be supplied to heat the carbon dioxide as well as the methane and steam reactants. Further, the carbon dioxide acts as a diluent, reducing the rate of the steam reforming reaction by reducing the interaction of the methane and water molecules. Steam reforming, like partial oxidation, involves significant heat transfer and loss of thermal energy to reduce the temperature of the synthesis gas product prior to its utilization to produce a liquid hydrocarbon (e.g. methanol) due to the high temperatures at which steam reforming must be effected—typically from 700° C. to 1000° C.

As a result of the difficulty of processing natural gas contaminated with carbon dioxide, carbon dioxide present in a carbon dioxide contaminated natural gas is generally separated from the hydrocarbon components of the natural gas prior to processing the natural gas to a liquid. As much carbon dioxide as possible is separated from the carbon dioxide contaminated natural gas, the goal being a carbon dioxide-free natural gas, since carbon dioxide is viewed as a contaminant, and is viewed as rendering processes inefficient or ineffective for producing liquid hydrocarbons (e.g. methanol) from the natural gas. Separation techniques include scrubbing the natural gas with a liquid chemical, e.g. an amine or methanol, to remove carbon dioxide, passing the natural gas through molecular sieves selective to separate carbon dioxide from the natural gas, and passing the natural gas through a membrane selective to separate carbon dioxide from the natural gas. These methods of separating carbon dioxide from a natural gas are effective for natural gases containing 40 vol. % or less of carbon dioxide, more typically 20 vol. % or less, but are either ineffective or commercially prohibitive in energy costs to separate carbon dioxide from natural gas when the natural gas is contaminated with greater than 40 vol. % of carbon dioxide.

Production of natural gas from natural gas fields containing natural gas contaminated with greater than 40 vol. % carbon dioxide is generally not undertaken due to the difficulty of producing liquid hydrocarbons (e.g. methanol) from natural gas contaminated with such large quantities of carbon dioxide and the difficulty of removing carbon dioxide from the natural gas when present in such a large quantity. However, some of the largest natural gas fields discovered to date are contaminated with high levels of carbon dioxide. Therefore, there is a need for an energy efficient, effective method to produce liquid hydrocarbons from a natural gas highly contaminated with carbon dioxide.

SUMMARY OF THE INVENTION

The present invention is directed to a process for recovering a natural gas contaminated with high levels of $CO_2$ and converting the natural gas into methanol, comprising:

a) extracting a gas comprising carbon dioxide and methane from a reservoir containing natural gas, where carbon dioxide comprises greater than 40 vol. % of the extracted gas;

b) scrubbing the extracted gas with a wash effective to produce a washed extracted gas containing less carbon dioxide than the extracted gas and to produce a carbon dioxide contaminated wash product, where the washed extracted gas contains at least 20 vol. % carbon dioxide and where the carbon dioxide contaminated wash product contains more carbon dioxide than the wash;

c) oxidizing the washed extracted gas with an oxygen containing gas in the presence of a partial oxidation catalyst at a temperature of 900° C. or less to produce an oxidation product gas containing hydrogen, carbon monoxide, and carbon dioxide, where the molar ratio of oxygen from the oxygen containing gas to carbon from the hydrocarbons in the extracted gas is less than one;

d) optionally contacting the oxidation product gas with steam and a water-gas shift catalyst at a temperature of from 200° C. to 400° C. and a pressure of from 0.1 MPa to 15 MPa to produce a water-gas shifted oxidation product gas;

e) contacting the oxidation product gas or the water-gas shifted oxidation product gas with a methanol synthesis catalyst at a temperature of from 200° C. to 300° C. and a pressure of from 5 MPa to 15 MPa to produce a methanol product gas comprising methanol and carbon dioxide; and f) separating a first liquid methanol product from the methanol product gas.

DETAILED DESCRIPTION OF THE INVENTION

The present invention provides a process for recovering a natural gas from a natural gas field contaminated with greater than 40 vol. % $CO_2$ and converting the recovered natural gas into liquid methanol. According to the process of the invention, natural gas contaminated with greater than 40 vol. % $CO_2$ is extracted from a natural gas field and is converted to an oxidation product gas including synthesis gas by catalytic partial oxidation where only a portion of the $CO_2$ is separated from the natural gas prior to the catalytic partial oxidation of the natural gas. The portion of $CO_2$ separated from the natural gas is selected so that the amount of $CO_2$ remaining in the natural gas is within a range optimal for improving the rate of production of methanol from a synthesis gas formed from the natural gas containing the $CO_2$. The amount of $CO_2$ left in the natural gas that is optimal for improving the rate of production of methanol from a synthesis gas formed from the natural gas is from 20 vol. % to 60 vol. %, or from 30 vol. % to 50 vol. %, or from 35 vol. % to 45 vol. %.

In an embodiment of the process of the present invention, the catalytic partial oxidation is effected at a temperature of less than 600° C. utilizing a catalyst having an activity sufficient to catalyze the partial oxidation of hydrocarbons in the natural gas at such temperatures in the presence of significant quantities of $CO_2$. In this embodiment, a relatively small amount of heat must be removed from the oxidation product gas containing the synthesis gas prior to reacting the oxidation product gas to produce a liquid methanol product—typically at most 300° C. As a result, little thermal energy is lost in heat exchange processes relative to conventional methods for processing natural gas into liquid methanol. The high levels of $CO_2$ present in the carbon dioxide contaminated natural gas (e.g. at least 20 vol. %) act as an oxidation reaction regulator to help maintain the temperature of the exothermic catalytic partial oxidation reaction below 600° C. The resulting oxidation product gas, including the $CO_2$ and synthesis gas, is then utilized to produce the liquid methanol product. The $CO_2$ is easily separated from the liquid methanol product by condensing the liquid methanol product and separating the condensate from the $CO_2$ containing gas.

In an embodiment of the process of the present invention, the portion of $CO_2$ removed from the carbon dioxide contaminated natural gas prior to partial oxidation of the natural gas is removed by washing the carbon dioxide contaminated natural gas with liquid methanol. The liquid methanol utilized to wash the carbon dioxide contaminated natural gas may be provided by separating a portion of the liquid methanol product and using the separated portion of the liquid methanol product as the methanol wash. Carbon dioxide may be subsequently removed from the carbon dioxide contaminated liquid methanol wash to recover the liquid methanol.

As used herein, when two or more elements are described as "operatively connected" or "operatively coupled", the elements are defined to be directly or indirectly connected. In the context of elements defining a flow path for a gas or a liquid, the term operatively connected or operatively coupled indicates that the designated elements are connected directly or indirectly to permit fluid or gas flow between the elements. In the context of elements for generating and/or consuming electricity, the term operatively connected or operatively coupled indicates that the designated elements are electrically connected either directly or indirectly.

As used herein, the term "natural gas" is defined as a gas containing one or more hydrocarbons that may contain additional non-hydrocarbon components including carbon dioxide, carbon monoxide, nitrogen, and hydrogen sulfide.

Figure 1:
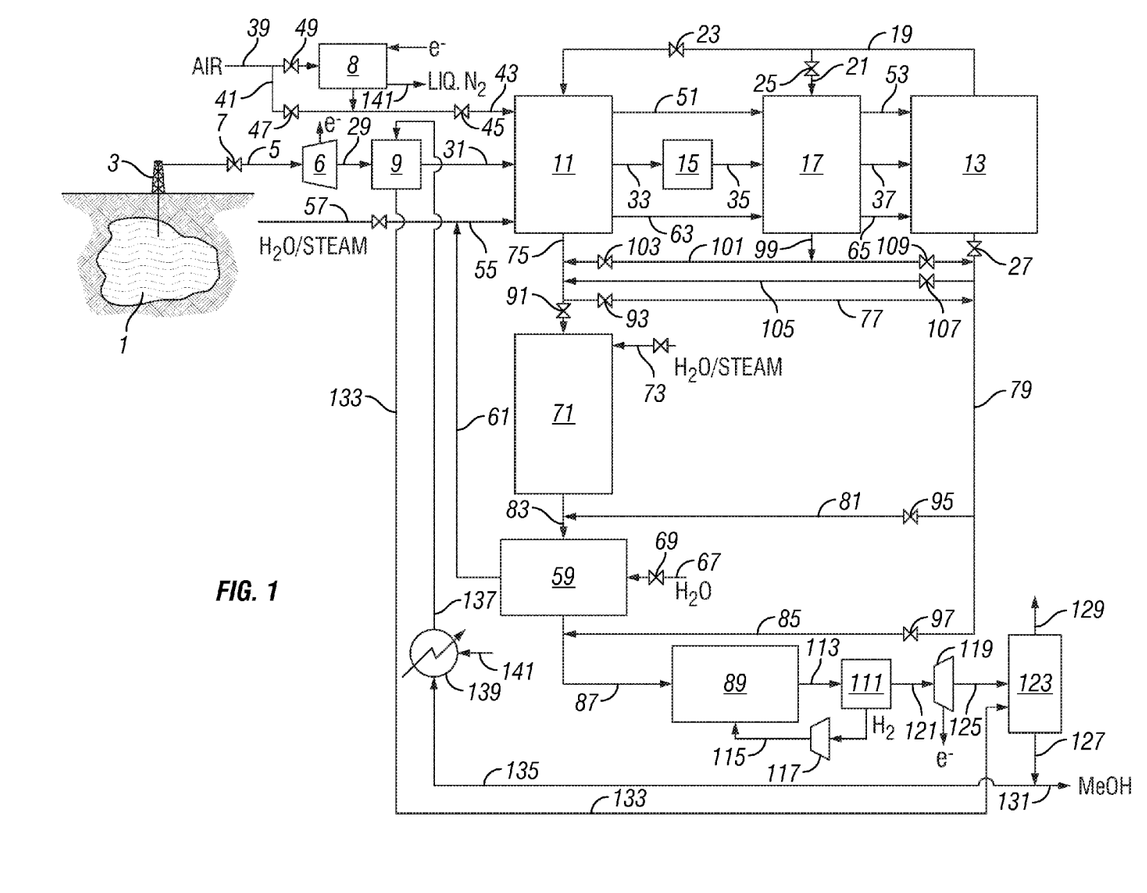
FIG. 1 is a schematic of a system that may be used to practice the process of the present invention.

Referring now to FIG. 1, which shows a system useful for practicing a process of the present invention, a process in accordance with the present invention will be described. Initially, a natural gas comprising methane and carbon dioxide is extracted from a natural gas reservoir 1, where the extracted gas contains greater than 40 vol. %, or greater than 50 vol. %, or at least 60 vol. %, or at least 70 vol. % carbon dioxide. The natural gas reservoir 1 may contain a natural gas comprising methane and carbon dioxide, where the carbon dioxide comprises greater than 40 vol. % of gas in the natural gas reservoir 1, or may contain a natural gas comprising methane and carbon dioxide where the carbon dioxide comprises 40 vol. % or less of the natural gas in the reservoir 1, but where the gas extracted from the reservoir 1 comprises greater than 40 vol.

% carbon dioxide. The gas extracted from the natural gas reservoir 1 may be extracted according to conventional methods for extracting a gas from a natural gas reservoir. In an embodiment, the gas may be extracted from the natural gas reservoir 1 by drilling a natural gas well 3 into the natural gas reservoir 1 and extracting the gas from the natural gas reservoir 1 through the well 3.

Conventional methods for assisting extraction of a gas from a natural gas reservoir may be utilized to aid in extraction of the gas from the reservoir 1, for example, acidizing and fracturing may be used to aid in extraction of the gas from the reservoir 1. The reservoir 1 may be acidized by injecting an acid, typically hydrochloric acid, into the reservoir through the well 3 to dissolve portions of rock in the reservoir 1 to increase flow of gas into and through the well 3. The reservoir 1 may be fractured to open the reservoir formation for increased gas flow by injecting a high pressure fluid or gas through the well 3 into the reservoir 1. The high pressure fluid or gas utilized for fracturing may be water or, in a preferred embodiment, carbon dioxide, where the carbon dioxide is provided from a by-product stream of the process of the present invention, as described below.

The gas extracted from the natural gas reservoir will contain methane and carbon dioxide, where the carbon dioxide comprises greater than 40 vol. % of the extracted gas. In an embodiment, the carbon dioxide may comprise greater than 50 vol. %, or at least 55 vol. %, or more than 60 vol. %, or at least 65 vol. %, or at least 70 vol. %, or at least 75 vol. %, or at least 80 vol. % of the extracted gas. The extracted gas may also contain other compounds, for example, the extracted gas may contain low molecular weight hydrocarbon gases other than methane such as ethane, propane, and butane, and may also contain gaseous sulfur containing compounds, for example, hydrogen sulfide.

The extracted gas forms a feedstock for a process for converting hydrocarbons, particularly methane, in the extracted gas to methanol. The process includes the steps of scrubbing the extracted gas with a wash to effective to produce a washed extracted gas containing less carbon dioxide than the extracted gas but at least 20 vol. % carbon dioxide, catalytically partially oxidizing the washed extracted gas to form an oxidation product gas containing synthesis gas, and subsequently, utilizing the oxidation product gas, or a derivative thereof, as a feedstock for producing a methanol product gas and subsequently condensing a liquid methanol product from the methanol product gas.

After extraction, the extracted gas is delivered to processing equipment effective to conduct the process of the invention. In an embodiment, line 5 and valve 7 may be used to control the flow of the extracted gas from the well 3 into the processing equipment.

The extracted gas may be conditioned prior to being catalytically partially oxidized. The extracted gas may be conditioned for catalytic partial oxidation by one or more steps including 1) depressurizing; 2) treating the extracted gas to remove carbon dioxide from the extracted gas, where the treatment to remove carbon dioxide from the extracted gas may be effective to remove minor amounts of contaminant gases such as propane, butane, and sulfur containing gases; 3) desulfurization of the extracted gas; and/or 4) heating the extracted gas. The one or more steps may be coordinated to provide optimal conditioning of the extracted gas for catalytic partial oxidation, for example, the extracted gas may be desulfurized in one or more steps in coordination with one or more heating steps.

The extracted gas will typically be at a relatively high pressure since natural gas extracted from a natural gas reservoir is generally a relatively high pressure gas. In an embodiment, the extracted gas may have a pressure of from 1 MPa to 30 MPa. In an embodiment, the extracted gas may have a pressure of from 5 MPa to 15 MPa which is within a preferred pressure range in which most of the steps of the process of the present invention are conducted, so that the pressure of the extracted gas need not be adjusted prior to feeding the extracted gas as a feedstock for catalytic partial oxidation.

In an embodiment, the extracted gas may be at very high pressure when extracted from the reservoir 1, for example, a pressure at or above 20 MPa, or at or above 15 MPa. The pressure of a very high pressure extracted gas may be reduced to a pressure more suitable for treatment in the process of the invention by expanding the very high pressure extracted gas to a selected pressure prior to catalytically partially oxidizing the extracted gas. In an embodiment, an extracted gas having a pressure above 15 MPa may be expanded to a pressure of from 1 MPa to 15 MPa, or to a pressure of from 5 MPa to 15 MPa, or to a pressure of 10 MPa.

A very high pressure extracted gas may be expanded by feeding the very high pressure extracted gas from line 5 through an expander 6, where the extracted gas may undergo a limited expansion to a pressure suitable for treatment of the extracted gas in the present process as described above. Energy may be produced by the limited expansion of a high pressure extracted gas through the expander 6, and the energy may be utilized to drive a unit 8 for separating oxygen from air, or, alternatively, may be captured as electricity.

In an embodiment, when the extracted gas has a pressure within from 1 MPa to 15 MPa upon extraction from the reservoir 1, no expansion of the extracted gas may be needed to reduce the pressure of the extracted gas in the process of the invention, and, therefore, the extracted gas need not be fed through an expander. In an embodiment, the expander 6 may optionally be excluded from the system for practicing the process of the invention.

In another embodiment, the extracted gas may have a significantly variable pressure, where the pressure of the extracted gas may range from a very high pressure, e.g. above 15 MPa, to a pressure below a very high pressure, e.g. from 1 MPa to 15 MPa. For example, the extracted gas may have a very high pressure when the gas is initially extracted from the reservoir 1 but the pressure of the gas extracted from the reservoir 1 may fall significantly over time as the reservoir 1 becomes depleted of gas. In this embodiment, the extracted gas may be expanded to a selected pressure when the pressure of the extracted gas is very high and expansion of the extracted gas may be avoided when the extracted gas has a pressure below a very high pressure. In this embodiment, the extracted gas may be fed through an expander 6 when the pressure of the extracted gas is very high, however, the extracted gas may be shunted around the expander 6 to avoid expansion of the extracted gas when the pressure of the extracted gas is below a very high pressure.

In the process of the present invention, the extracted gas is scrubbed with a wash in a scrubber 9 to remove a portion of the carbon dioxide from the extracted gas—producing a washed extracted gas containing less carbon dioxide than the extracted gas but containing at least 20 vol. % carbon dioxide. Although the mechanism is not completely understood, $CO_2$ apparently acts as an intermediate in the production of methanol from syngas and thereby improves the rate of production of the methanol.

The wash utilized to scrub the extracted gas may comprise liquid methanol, or may comprise a liquid amine, or may comprise a physical solvent such as SELEXOL® (a mixture of dimethyl ethers and polyethylene glycol) or PURISOL®

(N-methyl-2-pyrrolidone). Liquids containing amines effective to scrub the extracted gas may be selected from the group consisting of monoethanolamine (MEA), methyldiethanolamine, diethanolamine (MDEA), and mixtures thereof.

Figure 2:
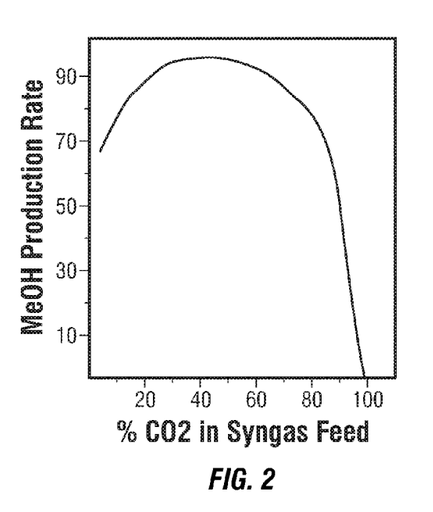
FIG. 2 is a graph showing a comparison of methanol conversion rate relative to carbon dioxide concentration in a synthesis gas from which the methanol is prepared.

As shown in FIG. 2, the rate of conversion of syngas to methanol according to the reaction $CO+2H_2 \leftrightarrows CH_3OH$ is optimal when $CO_2$ is present in the syngas in a range of from 20 vol. % to 60 vol. %, is more optimal when $CO_2$ is present in the syngas in a range from 30 vol. % to 50 vol. %, and is most optimal when $CO_2$ is present in the syngas in a range of from 35 vol. % to 45 vol. %. Therefore, the extracted gas is scrubbed with the wash in an amount effective to produce a washed extracted gas containing from 20 vol. % to 60 vol. % carbon dioxide, or in an amount effective to produce a washed extracted gas containing from 30 vol. % to 50 vol. % carbon dioxide, or in an amount effective to produce a washed extracted gas containing from 35 vol. % to 45 vol. % carbon dioxide. The amount of wash required to scrub the extracted gas to produce the desired level of carbon dioxide in the washed extracted gas may be determined by monitoring the carbon dioxide content (i.e. partial pressure) of the extracted gas fed into the scrubber 9 and calculating the amount of wash needed to remove a selected amount of carbon dioxide from the extracted gas based on the carbon dioxide content in the extracted gas feed and the temperature of the methanol wash.

Figure 3:
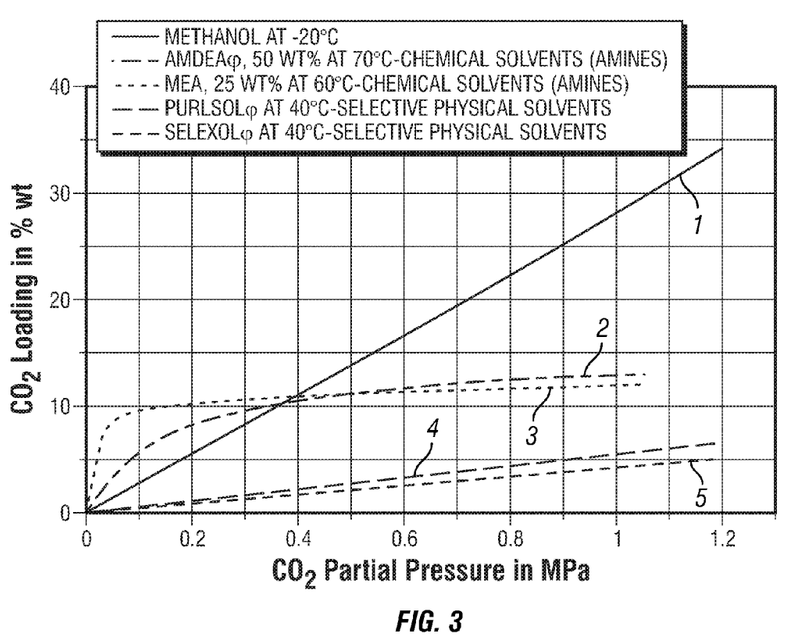
FIG. 3 is a graph showing the carbon dioxide loading of various washes relative to the partial pressure of carbon dioxide.

For example, FIG. 3 shows the carbon dioxide bulk removal capacity of methanol, monoethanolamine (MEA), methyldiethanolamine, diethanolamine (MDEA), PURISOL®, and SELEXOL® at selected temperatures relative to the partial pressure of carbon dioxide, which can be used to calculate the amount of wash required to remove a selected amount of carbon dioxide from the extracted feed to produce a desired carbon dioxide content in the washed extracted gas. Upon determination of the amount of wash required to remove the selected amount of carbon dioxide from the extracted gas, the selected amount of wash may be injected into the scrubber 9 to wash the extracted gas. In an embodiment, the monitoring of the extracted gas carbon dioxide content, the calculation of the amount of wash required to remove a selected amount of carbon dioxide from the extracted gas feed to produce a washed extracted gas with a selected carbon dioxide content, and injection of the required amount of wash into the scrubber 9 may be effected by an automated system, preferably an automated system controlled by one or more computers.

In a preferred embodiment, the wash utilized to scrub the extracted gas is comprises liquid methanol. The methanol wash used to remove a portion of the carbon dioxide from the extracted gas may chilled. In an embodiment, the methanol wash may have a temperature of from −40° C. to 0° C., or a temperature of from −30° C. to −15° C., or a temperature of −20° C.

As described in further detail below, the methanol wash used to scrub the extracted gas may be a portion of the liquid methanol product produced by the process of the present invention.

In addition to removing carbon dioxide from the extracted gas, the wash may be effective to remove non-methane, non-carbon dioxide gases from the extracted gas when such gases are present in the extracted gas in minor amounts. For example, the wash may remove propane, butane, and sulfur containing gases such as hydrogen sulfide from the extracted gas.

In an embodiment, the washed extracted gas may contain sulfur containing gas compounds when the wash in the scrubber 9 is ineffective to remove substantially all of the sulfur containing gas compounds from the extracted gas. The washed extracted gas containing sulfur containing gas compounds may be treated to reduce or eliminate such sulfur containing compounds from the washed extracted gas prior to catalytically partially oxidizing the washed extracted gas.

The washed extracted gas may be desulfurized in a desulfurizer 15 by contact with a solid sulfur adsorbing material, preferably disposed in a guard bed in the desulfurizer. Desulfurization of the washed extracted gas by contact with a solid sulfur adsorbing material may be conducted with conventional desulfurization materials for desulfurizing gases that are commercially available. In an embodiment of the process the solid desulfurization material is a commercially available material that acts as a sulfur adsorbent effective to adsorb sulfur from sulfur containing compounds that contact the material as the washed extracted gas is contacted with the material. Such sulfur adsorbing materials may include active metals including zinc oxide, copper oxide, aluminum oxide, a mixture of copper-zinc oxides, a mixture of copper-nickel oxides, and magnesium oxide, and nickel oxide and may include a support or binder formed of alumina, silica, alumina-silica, titania, or other refractory oxides.

The desulfurization is preferably conducted at a temperature at which sulfur in the sulfur containing compounds adsorbs to the solid desulfurization material but below a temperature at which sulfur adsorbed to the material is desorbed from the material. In an embodiment, the washed extracted gas may be contacted with a solid desulfurization material in the desulfurizer 15 at a temperature of from 100° C. to 350° C., more preferably at a temperature of from 150° C. to 300° C.

The washed extracted gas may be heated to a temperature effective to induce the partial oxidation of the extracted gas in the catalyst partial oxidation reactor. In an embodiment, the washed extracted gas may be heated in one or more heating elements prior to being fed to the catalytic partial oxidation reactor 13. More than one heating element may be used in the process of the invention to raise the temperature of the washed extracted gas to a selected temperature 1) to provide sufficient heating to raise the temperature of the washed extracted gas to the selected temperature, and/or 2) to permit other steps of the process, for example catalytic desulfurization, to be effected between the steps of initially heating the washed extracted gas in the first heating element and heating the washed extracted gas in any subsequent heating elements.

The washed extracted gas is heated to a temperature below the auto-ignition temperature of the washed extracted gas when combined with an oxygen containing gas in the catalytic partial oxidation reactor 13 in the presence of a partial oxidation catalyst so the washed extracted gas may be partially oxidized in the catalytic partial oxidation reactor 13. The reaction temperature of the washed extracted gas when combined with an oxygen-containing gas is, at least in part, dependent on the activity of the partial oxidation catalyst in the partial oxidation reactor 13, and may be a temperature of at least 200° C., preferably at least 300° C., and is a temperature of 900° C. or less, or may be a temperature of at most 800° C., or at most 700° C., or at most 600° C., or at most 500° C., or at most 400° C., and may be a temperature of from 200° C. to 900° C., or a temperature of from 250° C. to 700° C., or from 300° C. to 600° C. In an embodiment, the washed extracted gas may be heated to a temperature of from 200° C. to 900° C., or from 250° C. to 700° C., or from 300° C. to 600° C. by exchange of heat with the oxidation product gas formed by catalytic partial oxidation of the washed extracted gas. The reaction temperature, as used in this context, refers to a temperature that is sufficient to maintain a selected rate of reaction without destroying the catalyst or the reactor in which the reaction is effected.

The heating elements may be heat exchangers. The washed extracted gas may be heated in a first heat exchanger 11, or in a first heat exchanger 11 and a second heat exchanger 17, prior to being fed to the catalytic partial oxidation reactor 13. Preferably, heat from the catalytic partial oxidation of the washed extracted gas is used to heat the washed extracted gas by feeding the oxidation product gas from the catalytic partial oxidation reactor 13 through the first heat exchanger 11, and optionally through a second heat exchanger 17 if a second heat exchanger 17 is utilized, to heat the washed extracted gas prior to catalytically partially oxidizing the washed extracted gas. The catalytic partial oxidation reactor may be operatively connected in gaseous communication with the first heat exchanger 11 through line 19 and may be operatively connected in gaseous communication with the second heat exchanger 17 through lines 19 and 21, where valves 23, 25, and 27 control the flow of the oxidation product gas to the first and second heat exchangers 11 and 17. In an embodiment, valves 23, 25, and 27 may be automatically controlled in response to temperature measurements made of the washed extracted gas exiting the first heat exchanger 11, and/or of the washed extracted gas exiting the second heat exchanger 17, and/or of the oxidation product gas exiting the catalytic partial oxidation reactor 13 so that the temperature of the washed extracted gas and/or the oxidation product gas may be maintained at a selected level. Optionally, and less preferably, the washed extracted gas may be heated in the first heat exchanger 11, and optionally in a second heat exchanger 17 by passing steam through the first, and optionally second, heat exchangers to heat the washed extracted gas.

In an embodiment, the washed extracted gas may be heated to a temperature of from 100° C. to 350° C., or from 150° C. to 300° C. in a first heat exchanger 11, preferably by exchanging heat with a portion of the oxidation product gas from the catalytic partial oxidation reactor 13. Subsequently, either directly after heating the extracted gas in the first heat exchanger 11 or after one or more intervening process steps, the washed extracted gas may be heated to a temperature of from 200° C. up to 900° C., or from 250° C. to 700° C., or from 300° C. to 600° C. in one or more second heat exchangers 17, preferably by exchanging heat with a portion of the oxidation product gas from the catalytic partial oxidation reactor 13.

As noted above, the one or more steps of expanding, washing, desulfurizing, and heating the extracted gas may be coordinated to provide optimal conditioning of the washed extracted gas for catalytic partial oxidation. In a preferred embodiment, as shown in FIG. 1, the extracted gas may be initially expanded in expander 6 to a selected pressure, if expansion is necessary to reduce the pressure of the extracted gas to within a selected range. The extracted gas is then scrubbed with the methanol wash in scrubber 9 to adjust the carbon dioxide content of the extracted gas to a selected level and to remove a significant portion of sulfur containing compounds and other non-methane gases from the extracted gas. The washed extracted gas may then be heated in a first heat exchanger 11 to a temperature effective to permit catalytic desulfurization of the washed extracted gas, for example to a temperature of from 150° C. to 350° C. The washed extracted gas may then be catalytically desulfurized in desulfurizer 15 to remove most or all remaining sulfur containing compounds in the washed extracted gas. The washed extracted gas may then be heated in one or more second heat exchangers 17 to a temperature at or above the auto-ignition temperature of the washed extracted gas when mixed with an oxygen containing gas and contacted with a selected catalytic partial oxidation catalyst, preferably from 250° C. to 700° C. The heated washed extracted gas exiting the one or more second heat exchangers 17 may be fed to a catalytic partial oxidation reactor 13 for catalytic partial oxidation. In a particularly preferred embodiment, the oxidation product gas produced by catalytic partial oxidation of the washed extracted gas is utilized to provide heat for heat exchange with the washed extracted gas in the first and second heat exchangers 11 and 17.

The well 3, expander 6, if present, scrubber 9, first heat exchanger 11, desulfurizer 15, and the one or more second heat exchangers 17 may be operatively connected in gaseous communication by pipes or lines so the extracted gas may pass between the elements used to effect the steps of the process prior to catalytic partial oxidation of the washed extracted gas. For example, the expander 6 may be operatively connected in gaseous communication to the well 3 by line 5; the scrubber 9 may be operatively connected in gaseous communication with the expander 6 by line 29; the first heat exchanger 11 may be operatively connected in gaseous communication with the scrubber 9 by line 31; the desulfurizer 15 may be operatively connected in gaseous communication with the first heat exchanger by line 33; the second heat exchanger 17 may be operatively connected in gaseous communication with the desulfurizer 15 by line 35; and the catalytic partial oxidation reactor 13 may be operatively connected in gaseous communication with the second heat exchanger 17 by line 37.

An oxygen containing gas is also provided as a feed for the process for converting hydrocarbons in the washed extracted gas to methanol, where the oxygen containing gas is fed to the catalytic partial oxidation reactor 13 to partially oxidize the washed extracted gas upon contact with the catalytic partial oxidation catalyst at a temperature above the auto-ignition temperature of the mixture of the washed extracted gas and the oxygen containing gas. The oxygen containing gas may be air, a gas comprising at least 90 vol. % oxygen, or substantially pure oxygen comprising at least 99 vol. % oxygen.

In a preferred embodiment, the oxygen containing gas comprises at least 90 vol. % oxygen to avoid including substantial amounts of nitrogen in the process (e.g. if air were used as the oxygen containing gas), since nitrogen merely takes up reactor volume, and may produce undesirable $NO_x$ compounds in the catalytic partial oxidation of the washed extracted gas. An oxygen containing gas comprising at least 90 vol. % oxygen may be provided by separating oxygen from air in a unit for separating oxygen from air 8. The unit 8 may be a conventional air separation unit, or a conventional vacuum pressure swing absorption unit, or a unit in which oxygen may be separated from air by membranes. Preferably the oxygen containing gas provided for use in the catalytic partial oxidation of the washed extracted gas comprises at least 99 vol. % oxygen, and is provided by separating oxygen from air in a conventional air separation unit.

Energy ($e^-$) to drive the unit 8 for separating oxygen from air may be provided by expansion of a methanol product gas through an expander, as described in further detail below. If an expander 6 is used to reduce the pressure of the extracted gas, energy ($e^-$) produced by expansion of the extracted gas may also be used to drive the unit 8 to separate oxygen from air.

Nitrogen separated from the air in the air separation unit 8 may be cooled and collected as liquid nitrogen in the air separation unit 8. The liquid nitrogen may be used to cool various gas streams in the present process by exchanging heat with the gas stream to be cooled or by exchanging heat with a portion of the liquid methanol product, as described in further detail below.

The oxygen-containing gas may be compressed to a pressure within a range from 1 MPa to 15 MPa, or from 5 MPa to 15 MPa, or to 10 MPa. In an embodiment, the oxygen-containing gas is compressed to a pressure within 1 MPa of the pressure of the washed extracted gas after any expansion of the extracted gas is effected. Energy ($e^-$) to compress the oxygen-containing gas may be provided by expansion of the methanol product gas through an expander, as described in further detail below. If an expander 6 is used to reduce the pressure of the extracted gas, energy ($e^-$) produced by the expansion of the extracted gas may also be used to compress the oxygen-containing gas.

The oxygen containing gas is heated to a temperature at or above the auto-ignition temperature of the combined washed extracted gas and oxygen containing gas in the catalytic partial oxidation reactor 13 in the presence of a partial oxidation catalyst so the washed extracted gas may be partially oxidized in the catalytic partial oxidation reactor 13. As noted above with respect to the washed extracted gas, the auto-ignition temperature of the washed extracted gas when combined with an oxygen-containing gas is, at least in part, dependent on the activity of the partial oxidation catalyst in the partial oxidation reactor 13, and may be a temperature of at least 200° C., preferably at least 300° C., and is a temperature of 900° C. or less, or at most 800° C., or at most 700° C., or at most 600° C., or at most 500° C., or at most 400° C., and may be a temperature of from 200° C. to 900° C., or a temperature of from 250° C. to 700° C., or from 300° C. to 600° C.

The oxygen-containing gas may be heated in one or more heaters to a selected temperature at or above the auto-ignition temperature of the combined washed extracted gas and oxygen-containing gas in the presence of a selected partial oxidation catalyst. The one or more heaters may be conventional heaters for heating a gas, including electrical heaters and heat exchangers. In a preferred embodiment, the heaters for heating the oxygen containing gas are heat exchangers. In an embodiment, the oxygen-containing gas may be heated to a temperature of from 100° C. to 350° C., or from 150° C. to 300° C. in a first heat exchanger 11, preferably by exchanging heat with a portion of the oxidation product gas from the catalytic partial oxidation reactor 13. Subsequently, the oxygen-containing gas may be heated to a temperature of from 200° C. to 900° C., or from 250° C. to 700° C., or from 300° C. to 600° C. in one or more second heat exchangers 17, preferably by exchanging heat with a portion of the oxidation product gas from the catalytic partial oxidation reactor 13.

The oxygen-containing gas is mixed with the washed extracted gas in an amount effective to partially, but not fully, oxidize the hydrocarbons in the washed extracted gas upon catalyst-induced reaction of the mixture. Therefore, the oxygen-containing gas is mixed with the washed extracted gas in an amount such that the molar ratio of oxygen from the oxygen containing gas to carbon from the hydrocarbons of the washed extracted gas is less than one. Preferably, the oxygen-containing gas is mixed with the washed extracted gas in an amount such that the molar ratio of oxygen from the oxygen containing gas to carbon from the hydrocarbons in the washed extracted gas is at least 0.4 or at least 0.5, or at least 0.6, or at least 0.65, and is at most 0.99, or at most 0.95, or at most 0.90, or at most 0.85.

As shown in FIG. 1, air may be provided as an input stream through line 39. The air may be provided as the oxygen containing gas through line 41, or the air may be fed to a unit 8 for separating oxygen from air or for enriching the oxygen content of air, as described above. The oxygen containing gas, either air, oxygen enriched air, or substantially oxygen, may be fed to the first heat exchanger through line 43. Valve 45 may be used to control the rate that the oxygen containing gas is introduced into the process, in particular, to maintain the molar ratio of oxygen in the oxygen containing gas to carbon from the hydrocarbons in the extracted gas to less than one. Valves 47 and 49 may be used to direct the flow of the air input stream to the oxygen separation unit 8 or around the unit 8.

The oxygen containing gas may be heated in the first heat exchanger 11 by exchanging heat with the oxidation product gas from the catalytic partial oxidation of the oxygen containing gas and the washed extraction gas, and may subsequently be fed to one or more second heat exchangers 17 through line 51 for further heating by exchange of heat with the oxidation product gas in order to raise the temperature of the oxygen containing gas to a temperature at or above the auto-ignition temperature of the oxygen-containing gas and the washed extracted gas in the presence of a selected partial oxidation catalyst. The oxygen containing gas may then be fed from the one or more second heat exchangers 17 to the catalytic partial oxidation reactor 13 for catalytically-induced reaction with the washed extracted gas through line 53, or may be mixed with the heated washed extracted gas exiting the one or more second heat exchangers 17 prior to feeding the mixture to the catalytic partial oxidation reactor 13 for reaction. Optionally, though less preferably, the oxygen-containing gas and the washed extracted gas may be mixed prior to heating and may be heated together, or may be mixed after initially heating each gas separately, e.g. in the first heat exchanger 11, but prior to further heating, e.g. in the one or more second heat exchangers 17—where the mixture is ultimately fed to the catalytic partial oxidation reactor 13 for contact with a partial oxidation catalyst to induce reaction of the mixture.

In an embodiment, steam may be mixed with the oxygen containing gas and the washed extracted gas prior to or during reaction of the oxygen containing gas and the washed extracted gas. The steam may serve to inhibit the formation of carbon deposits in the catalytic partial oxidation reactor 13 and/or on the partial oxidation catalyst. In an embodiment, steam may mixed with the oxygen containing gas and the washed extracted gas prior to or during partial oxidation reaction of the oxygen containing gas and the washed extracted gas to autothermally reform the steam and a portion of methane in the extracted gas according to the following reaction: $2CH_4+O_2+H_2O \rightarrow 5H_2+CO$. When steam is added for the purpose of autothermal reformation, the steam may be added to the mixture of the washed extracted gas and the oxygen containing gas in an amount such that the steam is present in the mixture in an amount of up to 13 wt. % of the mixture. When steam is utilized for the purpose of autothermal reformation, the amount of steam mixed with the washed extracted gas and the oxygen containing gas is selected to provide a molar ratio of steam to carbon from hydrocarbons in the washed extracted gas ($H_2O/C_{HC}$) of greater than 0 and less than 0.4.

If utilized, steam may be compressed to a pressure within a range from 1 MPa to 15 MPa, or from 5 MPa to 15 MPa, or to 10 MPa. In an embodiment, the steam is compressed to a pressure within 1 MPa of the pressure of the washed extracted gas after any expansion of the extracted gas is effected. Energy ($e^-$) to compress the steam may be provided by expansion of the methanol product gas through an expander, as described in further detail below. If an expander 6 is used to reduce the pressure of the extracted gas, energy (e⁻) produced by the expansion of the extracted gas may also be used to compress the steam.

Water or steam may be fed to one or more heaters or heat exchangers to heat the steam to a temperature of from at least 200° C., preferably at least 300° C., and to a temperature of 900° C. or less, or at most 800° C., or at most 700° C., or at most 600° C., or at most 500° C., or at most 400° C., where the temperature may be a temperature of from 200° C. to 900° C., or a temperature of from 250° C. to 700° C., or from 300° C. to 600° C.

In a preferred embodiment, water or steam may be fed to the first heat exchanger 11 through line 55. Water or steam may be fed into the process through an inlet line 57 operatively coupled to line 55, or may be fed from a third heat exchanger 59, optionally used to cool the oxidation product gas or its water-gas shifted product as described below, through line 61 which may be operatively connected to line 55. The water or steam may be heated to produce heated steam in the first heat exchanger 11 by exchange of heat with the oxidation product gas produced by the catalytic partial oxidation of the oxygen containing gas and the extracted gas. The heated steam may be fed from the first heat exchanger 11 to the one or more second heat exchangers 17 through line 63 for further heating, or optionally may be fed directly into the catalytic partial oxidation reactor 13 for mixing with the oxygen containing gas and the washed extracted gas during reaction, or may be mixed with either or both the oxygen containing gas and/or the washed extracted gas prior to feeding the mixture to the catalytic partial oxidation reactor 13 for reaction. If the steam is fed to the one or more second heat exchangers 17 for further heating, the steam may be heated further in the one or more second heat exchangers by exchanging heat with a portion of the oxidation product gas. The resulting steam may be fed directly to the catalytic partial oxidation reactor 13 from the one or more second heat exchangers 17 through line 65, or the steam may be mixed with either or both the oxygen containing gas and/or the washed extracted gas prior to feeding the mixture to the catalytic partial oxidation reactor 13 for reaction.

The heated oxygen containing gas and the heated washed extracted gas, if not previously mixed, may be mixed upon introduction into the catalytic partial oxidation reactor 13. The mixture, regardless of when mixed, is then reacted in an exothermic catalytic partial oxidation reaction to produce an oxidation product gas, optionally in the presence of steam, in the catalytic partial oxidation reactor 13. The oxidation product gas contains the reaction products from the reaction of oxygen in the oxygen containing gas and hydrocarbons, particularly methane, in the washed extracted gas, plus the carbon dioxide present in the washed extracted gas—which is substantially unreactive but retards the oxidation reaction sufficiently to maintain the temperature of the oxidation product gas at 900° C. or less, or 800° C. or less, or 700° C. or less, or below 600° C. The oxygen in the oxygen containing gas and the methane in the washed extraction gas react as follows:

$$CH_4 + \tfrac{1}{2}O_2 \rightarrow CO + 2H_2$$

where the reaction product is primarily a synthesis gas comprising hydrogen and carbon monoxide, where hydrogen is present in a 2:1 molar ratio relative to carbon monoxide. The oxidation product gas, therefore, contains hydrogen, carbon monoxide, and carbon dioxide as its main constituents, and optionally contains steam if steam was added to the mixture of the washed extracted gas and the oxygen-containing gas.

The oxidation reaction is maintained at a low temperature such that the oxidation product gas exiting the catalytic partial oxidation reactor has a temperature of 900° C. or less, or at most 800° C., or at most 700° C., or below 600° C. The temperature of the oxidation reaction is maintained at a temperature of 900° C. or less, or at most 800° C. or at most 700° C., or below 600° C. by 1) controlling the temperature of the washed extracted gas and/or oxygen containing gas feeds to be mixed and reacted, where the feed temperatures of the washed extracted gas and/or oxygen containing gas may be lowered to reduce the temperature of the oxidation product gas; and/or 2) controlling the temperature of any steam added to the reaction mixture to regulate the reaction temperature, where the feed temperature of steam added to the reaction mixture may be lowered to reduce the temperature of the oxidation product gas; and/or 3) adjusting the molar ratio of oxygen in the oxygen containing gas to carbon in hydrocarbons in the washed extracted gas, where the ratio of oxygen in the oxygen containing gas to carbon in hydrocarbons in the extracted gas may lowered to reduce the temperature of the oxidation product gas; and/or 4) adjusting the ratio of the feed rate of the oxygen containing gas to the washed extracted gas to decrease the amount of oxygen containing gas relative to the washed extracted gas present in the reaction and thereby increase the overall carbon dioxide concentration present in the reaction to reduce the temperature of the oxidation product gas.

The partial oxidation of the hydrocarbons present in the washed extracted gas is effected by mixing the washed extracted gas and the oxygen containing gas, and optionally steam, and contacting the mixture of washed extracted gas and oxygen containing gas with a catalytic partial oxidation catalyst, where the mixture has a temperature of from 200° C. up to 900° C. Preferably the catalytic partial oxidation catalyst is highly reactive, and the partial oxidation is effected by contacting the mixture of washed extracted gas and oxygen containing gas with the highly reactive catalyst where the mixture has a temperature of from 200° C. up to 600° C. As discussed above, the washed extracted gas and the oxygen containing gas, and optionally steam, may be mixed prior to being fed to the catalytic partial oxidation reactor 13. Alternatively, the washed extracted gas and the oxygen containing gas, and optionally steam, may be initially mixed in the catalytic partial oxidation reactor 13 prior to contacting the catalyst.

The partial oxidation of the hydrocarbons present in the washed extracted gas may be conducted at an elevated pressure. In an embodiment, the pressure at which the mixture of washed extracted gas and the oxygen-containing gas, and optionally steam, may be reacted may range from 1.5 MPa to 15 MPa, or from 5 MPa to 15 MPa, or at 10 MPa. The pressure of the mixture of washed extracted gas, the oxygen-containing gas, and optionally steam, is determined by the pressure of the individual component gases, which may be controlled as described above.

The catalyst utilized to effect the partial oxidation of the mixture of hydrocarbons in the extracted gas and oxygen in the oxygen containing gas must have sufficient catalytic activity to effect oxidation (partial) of hydrocarbons, particularly methane, in the mixture at a temperature of from 200° C. up to 900° C., or at a temperature of from 250° C. to 700° C., or at a temperature of from 300° C. to 600° C. "Sufficient catalytic activity", as used with respect to the partial oxidation catalyst is defined as: catalytic activity sufficient to effect partial oxidation of at least 85 mol % of hydrocarbons in the washed extracted gas at a gas hourly space velocity of at least 20,000 NL/kg/h (expressed as normal liters of gas per kilogram of catalyst per hour, wherein normal liters refers to liters under STP conditions, i.e. 25° C. and 1 atm.).

The catalyst utilized in the process of the present invention to effect the partial oxidation reaction of the mixture of the washed extracted gas and the oxygen containing gas may be a conventional partial oxidation catalyst having sufficient catalytic activity to effect oxidation (partial) of hydrocarbons, particularly methane in the mixture at a temperature of from 700° C. to 900° C. Alternatively, and more preferably, the catalyst utilized in the process of the present invention to effect the partial oxidation reaction of the mixture of the washed extracted gas and the oxygen containing gas is a highly reactive partial oxidation catalyst having sufficient catalytic activity to effect oxidation (partial) of hydrocarbons, particularly methane, in the mixture at a temperature of from 200° C. to 700° C., or from 300° C. up to 600° C. Use of a highly reactive partial oxidation catalyst having sufficient catalytic activity to effect partial oxidation of hydrocarbons at temperatures of 700° C. or less, or at temperatures up to 600° C., is preferred in the process of the present invention 1) since the carbon dioxide present in the washed extracted gas may be used to control the temperature of the exothermic partial oxidation reaction to temperatures of 700° C. or less or up to 600° C., and 2) to reduce thermal energy loss relative to catalytic partial oxidation effected at higher temperatures.

Such highly reactive partial oxidation catalysts may comprise one or more catalytically active metals selected from the group consisting of rhodium, iridium, ruthenium, and platinum. Highly reactive partial oxidation catalysts comprising rhodium and/or iridium are preferred. The catalytically active metals of a highly reactive partial oxidation catalyst may be intimately associated as an admixture when two or more of the metals are present in the catalyst so each metal may affect the catalytic performance or stability of one or more other metals present in the catalyst. As used herein, the catalytically active metals of the catalyst are "intimately associated as an admixture" when at least 50%, or at least 90% of each catalytically active metal is present as part of the catalyst within a distance of 10 μm, or within a distance of 5 μm, of at least one of the other catalytically active metals. The admixture of catalytically active metals may be an alloy of the metals— where the presence of an alloy can be determined by methods known in the art, for example by XRD. In an embodiment, a highly reactive partial oxidation catalyst that may be used in the process of the invention utilizes an alloy of rhodium and iridium to provide catalytic activity in the catalytic partial oxidation reaction of the mixture of the washed extracted gas and the oxygen containing gas. In an embodiment, the catalyst for effecting the partial oxidation reaction of the mixture of the washed extracted gas and the oxygen containing gas may comprise rhodium and iridium in the form of wires or gauzes of a rhodium-iridium alloy.

The one or more catalytically active metals of the partial oxidation catalyst may be supported on a catalyst carrier material. Suitable catalyst carrier materials are known in the art and include metals and refractory oxides such as silica, alumina, titania, zirconia, and mixtures thereof. High-alloy alumina containing steel, such as FeCrALLOY®-type materials are suitable metals for the catalyst carrier. Zirconia-based refractory oxides, particularly including at least 70 wt. % zirconia, are preferred refractory oxide materials for the catalyst carrier. Such zirconia-based refractory oxides may be stabilized or partially stabilized by one or more oxides of Mg, Ca, Al, Y, La, or Ce. Particularly suitable carrier materials are Ce-ZTA (zirconia-toughened alumina) and Y-PSZ (partially stabilized zirconia), both commercially available. Structured ceramic supports having a honeycomb-like structure may also be used as the catalyst carrier.

The one or more catalytically active metals of the partial oxidation catalyst may be deposited on the catalyst carrier material by techniques known in the art. In one embodiment, the one or more catalytically active metals of the partial oxidation catalyst may be deposited on the catalyst carrier material by impregnation. The carrier may be impregnated with one or more solutions of the one or more catalytically active metals, then the carrier impregnated with the one or more catalytically active metals may be dried to form the catalyst, and then, optionally, the dried catalyst may be calcined. If the catalyst comprises more than one catalytically active metal, the catalytically active metals may be combined in one solution for impregnating the carrier, or, optionally, the carrier may be impregnated with separate solutions of each catalytically active metal sequentially. In another embodiment, the one or more catalytically active metals may be deposited on the catalyst carrier by wash coating.

The partial oxidation catalyst comprises one or more catalytically active metals in any suitable amount to achieve the required catalytic activity to enable the reaction of the mixture of the oxygen containing gas and the washed extracted gas at a temperature 900° C. or less, or at most 800° C., or at most 700° C., or at most 600° C., or at most 500° C., or at most 400° C. In an embodiment, the partial oxidation catalyst comprises from 0.02 wt. % to 10 wt. %, or from 0.1 wt. % to 7.5 wt. %, of the one or more catalytically active metals. In an embodiment, the partial oxidation catalyst comprises rhodium and iridium as catalytically active metals where the rhodium and iridium comprise from 0.02 wt. % to 10 wt. % of the partial oxidation catalyst, and the rhodium-to-iridium weight ratio may be in the range of from 0.1 to 10, or from 0.2 to 5, or from 0.5 to 2.

The catalytically active metals of the partial oxidation catalyst may be associated with one or more inorganic metal cations. The one or more inorganic metal cations may be selected from Columns 2, 3, 4, 13, and 14 of the Periodic Table and the lanthanides, for example, Al, Mg, Zr, Ti, La, Hf, Si, and Ba, where Zr is preferred. The one or more inorganic metal cations may be intimately associated in an admixture with the one or more catalytically active metals of the partial oxidation catalyst, where the cation to catalytically active metal ratio may be in excess of or equal to 1.0, or 2.0, or 3.0 at the surface of the catalyst.

The partial oxidation catalyst used in the process of the present invention may be in any form accessible for a mixture of the washed extracted gas and the oxygen containing gas, and optionally steam, to contact the one or more catalytically active metals, and optionally the associated one or more inorganic metal cations, so that a partial oxidation reaction of the mixture may be effected. For example, the partial oxidation catalyst may be in the form of a porous monolithic structure such as a honeycomb or a foam, a fixed bed of catalyst particles, an arrangement of metal wire or gauze, or combinations thereof.

Catalysts effective for use as the partial oxidation catalyst in the process of the present invention are available commercially, for example, from CRI Catalyst Company, 16825 Northchase Drive, Houston, Tex. 77060, USA.

After catalytic partial oxidation of the mixture of the washed extracted gas and the oxygen containing gas, and optionally steam, the oxidation product gas is removed from the catalytic partial oxidation reactor 13. As noted above, the oxidation product gas may have a temperature of up to 900° C., and is comprised of hydrogen, carbon monoxide, and carbon dioxide, and optionally steam.

The oxidation product gas is used as a feedstock for a methanolation reaction to produce methanol.

The oxidation product gas may be conditioned prior to being utilized as a feedstock for producing methanol. The oxidation product gas may be conditioned by one or more optional steps, including 1) cooling the oxidation product gas; and 2) effecting a water-gas shift reaction using the oxidation product gas as a feedstock to increase the hydrogen content of the oxidation product gas.

The oxidation product gas may be cooled in one or more steps to adjust the temperature of the oxidation product gas to a temperature suitable for converting the oxidation product gas to methanol, and, optionally, to a temperature suitable for effecting a water-gas shift reaction in the oxidation product gas prior to converting the oxidation product gas to methanol. The oxidation product gas may have a temperature of from 200° C. up to 900° C., or from 400° C. up to 800° C., or from 500° C. up to 600° C. In the process of the invention, the hydrogen content of the oxidation product gas may be increased in a water-gas shift reaction which may be effected at a selected temperature in the range of from 200° C. to 400° C., and if the temperature of the oxidation product gas is above a selected temperature for effecting a water-gas shift reaction, the oxidation product gas may be cooled to the selected temperature. Further, in the process of the invention, the oxidation product gas or its water-gas shifted product (the water-gas shifted oxidation product gas) is converted to methanol a selected temperature in the range of from 200° C. to 300° C., therefore, if the oxidation product gas or its water-gas shifted product has a temperature above a selected temperature for converting the oxidation product gas or the water-gas shifted oxidation product gas to methanol, the oxidation product gas or its water-gas shifted product must be cooled to the selected temperature. In an embodiment of the process of the present invention, the oxidation product gas, as either the oxidation product gas itself or as the oxidation product gas and/or its water-gas shifted product gas, may be cooled at most 700° C., or at most 600° C., or at most 500° C., or at most 400° C., or at most 300° C., or at most 200° C., or at most 150° C. prior to converting the oxidation product gas or water-gas shifted oxidation product gas to methanol.

In a preferred embodiment, as described above, the oxidation product gas may be cooled by exchanging heat with the washed extracted gas, and/or the oxygen containing gas, and/or steam in the first heat exchanger 11 and/or the one or more second heat exchangers 17. The oxidation product gas may be cooled by up to 700° C., or up to 600° C., or up to 500° C., or up to 400° C., or up to 300° C., or up to 250° C., or up to 200° C., or up to 150° C. in the first heat exchanger 11 and/or the one or more second heat exchangers 17. In an embodiment, the oxidation product gas produced by the catalytic partial oxidation reaction of the mixture of the washed extracted gas and the oxygen containing gas, and optionally steam, has a temperature of from 400° C. up to 900° C. prior to being cooled by exchanging heat with the extracted gas and/or the oxygen containing gas and/or steam in either the first heat exchanger 11 and/or the one or more second heat exchangers 17, and has a temperature of from 200° C. to 500° C., or from 250° C. to 400° C. after being cooled by such heat exchange.

In an embodiment, the oxidation product gas or its water-gas shifted product may be cooled by heat exchange with water, steam, liquid nitrogen from the air separation unit 8, or other coolant in one or more third heat exchangers 59, preferably by at most 500° C., or at most 400° C. or at most 300° C., or at most 200° C., or at most 100° C. In an embodiment, the oxidation product gas or its water-gas shifted product is not cooled by heat exchange with the washed extracted gas, or the oxygen containing gas, or water/steam in the first heat exchanger 11 or the one or more second heat exchangers 17, but is cooled by heat exchange with water, steam, liquid nitrogen from the air separation unit 8, or other coolant in the one or more third heat exchangers 59. More preferably, the oxidation product gas is cooled by heat exchange with the washed extracted gas and/or the oxygen-containing gas and/or water/steam in the first heat exchanger 11 and/or the one or more second heat exchangers 17 and subsequently the cooled oxidation product gas or its water-gas shifted product gas is cooled by exchange of heat with water, steam, liquid nitrogen from the air separation unit 8, or other coolant in the one or more third heat exchangers 59.

Water, steam, liquid nitrogen from the air separation unit 8, or other coolant may be fed to the one or more third heat exchangers 59 through inlet line 67 at a flow rate sufficient to cool the oxidation product gas or water-gas shifted oxidation product gas to a selected temperature. The flow rate of the water, steam, liquid nitrogen, or other coolant to the one or more third heat exchangers 59 may be controlled by adjusting a third heat exchanger coolant inlet valve 69. In an embodiment, heated steam produced from cooling the oxidation product gas or the water-gas shifted oxidation product gas in the one or more third heat exchangers 59 may be fed to the first heat exchanger through lines 61 and 55 to cool the oxidation product gas in the first heat exchanger 11 and subsequently in the one or more second heat exchangers 17, and to be mixed with the washed extracted gas and the oxygen-containing gas in the catalytic partial oxidation reaction.

In an embodiment, the hydrogen content of the oxidation product gas may be increased by contacting the oxidation product gas, a water-gas shift catalyst, and steam at a temperature of from 200° C. to 400° C. in a water-gas shift reactor 71, where additional steam may be fed into the water-gas shift reactor 71 through steam inlet line 73. Contact of the oxidation product gas, a water-gas shift catalyst, and steam at a temperature of from 200° C. to 400° C. in the water gas shift reactor 71 converts carbon monoxide and steam to hydrogen and carbon dioxide as follows:

$$CO + H_2O \leftrightharpoons CO_2 + H_2$$

where the production of hydrogen is energetically favored at temperatures in the range of from 200° C. to 400° C. despite the presence of excess carbon dioxide in the oxidation product gas. The temperature at which the oxidation product gas is contacted with the water-gas shift catalyst to effect the reaction may be selected to adjust the relative molar ratio of carbon monoxide to hydrogen, where lower temperatures within the range of 200° C. to 400° C. result in higher conversion of carbon monoxide to carbon dioxide and thus a higher molar hydrogen to carbon monoxide ratio, and higher temperatures in this temperature range result in lower conversion of carbon monoxide to carbon dioxide and thus a lower molar hydrogen to carbon monoxide ratio than water-gas shift reactions run at lower temperatures within the temperature range. The presence of carbon dioxide in the oxidation product gas helps inhibit the reaction going to completion and converting all carbon monoxide present in the oxidation product gas to hydrogen so that the water-gas shifted oxidation product gas may be utilized as a feed to produce methanol. The water-gas shifted oxidation product gas may contain primarily hydrogen, carbon monoxide, carbon dioxide and steam.

The water-gas shift catalyst contacted with the oxidation product gas to produce the water-gas shifted oxidation product gas may be a commercially available conventional water-gas shift catalyst. The water-gas shift catalyst may comprise a catalytically active transition metal or transition metal oxide selected from the group consisting of Fe, Zn, Cr, Cu, Ni, Co, their oxides, and mixtures thereof. The catalytically active transition metal or transition metal oxide may be supported on an alumina, titania, zirconia, and/or silica support. In an embodiment, the water-gas shift catalyst may be chromium-promoted magnetite ($Fe_3O_4$), particularly for shift reactions effected at temperatures from 350° C. to 400° C., or in another embodiment the catalyst may contain a mixture of CuO (30-70 wt. %), ZnO (20-50 wt. %), and $Al_2O_3$ (5-40 wt. %), particularly for shift reactions effected at temperatures of from 200° C. to 350° C. Preferably the water-gas shift catalyst is supported in a fixed bed in the shift reactor 71.

The system for conducting the process of the present invention may be configured for conducting the process optimally, depending on the cooling and/or heat exchange required and the relative hydrogen and carbon monoxide content of the oxidation product gas to be used as a feedstock to produce methanol. As noted above, the oxidation product gas may be fed from the catalytic partial oxidation reactor 13 to the first heat exchanger 11 and/or the one or more second heat exchangers 17 for heat exchange with the washed extracted gas, the oxygen containing gas, and optionally steam, through lines 19 and 21, where valves 23 and 25 may be used to control the flow of the oxidation product gas to the respective first and second heat exchangers 11 and 17. In an embodiment (not shown) the oxidation product gas may be fed from the catalytic partial oxidation reactor to the second heat exchanger for heat exchange with the washed extracted gas, the oxygen-containing gas, and optionally steam, and the cooled oxidation product gas exiting the second heat exchanger may be fed to the first heat exchanger for further cooling by exchanging heat with the washed extracted gas, the oxygen-containing gas, and optionally steam.

The cooled oxidation product gas exiting the first heat exchanger 11 may be fed to the water-gas shift reactor 71 through line 75, or, may be fed to the one or more third heat exchangers 59 through lines 77, 79, 81, and 83 without passing the cooled oxidation product gas through the water gas shift reactor 71, or may be passed directly to reactor 89 for converting the oxidation product gas to a methanol gas product through lines 75, 77, 79, 85, and 87 without passing the cooled oxidation product gas through the water gas shift reactor 71 or the one or more third heat exchangers 59. Valves 91, 93, 95, and 97 may be adjusted to control the flow of the oxidation product gas from the first heat exchanger 11 to the water-gas shift reactor 71, the one or more third heat exchangers 59, or to the reactor 89.

Similarly, the cooled oxidation product gas exiting the second heat exchanger 17 may be fed to the water-gas shift reactor 71 through lines 99, 101, and 75, or, may be fed to the one or more third heat exchangers 59 through lines 99, 101, 79, 81 and 83 without passing the cooled oxidation product gas through the water-gas shift reactor 71, or, may be passed directly to reactor 89 for converting the cooled oxidation product gas to a methanol product gas through lines 99, 101, 79, 85, and 87 without passing the cooled oxidation product gas through the water-gas shift reactor 71 or the one or more third heat exchangers 59. Valves 103, 109, 95, and 97 may be adjusted to control the flow of the oxidation product gas from the second heat exchanger 17 to the water-gas shift reactor 71, the one or more third heat exchangers 59, or to the reactor 89.

Optionally, but less preferably, the oxidation product gas is not cooled by heat exchange with the washed extracted gas and the oxygen-containing gas, and optionally steam, in the first and second heat exchangers 11 and 17, but is fed directly from the catalytic partial oxidation reactor 13 to either the water-gas shift reactor 71, or the one or more third heat exchangers 59, or the reactor 89 for converting the oxidation product gas to a methanol gas product. The oxidation product gas may be fed directly from the catalytic partial oxidation reactor 13 to the water-gas shift reactor 71 when the temperature of the oxidation product gas is from 200° C. to 400° C. and it is desirable to increase the molar ratio of hydrogen to carbon monoxide in the oxidation product gas. The oxidation product gas may be fed directly from the catalytic partial oxidation reactor 13 to the reactor 89 when the oxidation product gas has a temperature of from 200° C. to 300° C. to produce a methanol product gas. The oxidation product gas may be fed directly to the one or more third heat exchangers 59 when increasing the molar ratio of hydrogen to carbon monoxide is not desired and when the oxidation product gas may be cooled sufficiently in the third heat exchanger 59 so that the cooled oxidation product gas has a temperature of from 200° C. to 300° C.

The oxidation product gas may be fed directly from the catalytic partial oxidation reactor 13 to the water-gas shift reactor 71, or the one or more third heat exchangers 59, or the reactor 89 by directing the flow of the oxidation product gas to the selected element while precluding flow of the oxidation product gas to the first and second heat exchangers 11 and 17. The oxidation product gas may be directed from the catalytic partial oxidation reactor 13 to the water-gas shift reactor through lines 79 and 105, where valves 27, 93, 95, 97, 107 and 109 may be adjusted to control the flow of the oxidation product gas from the catalytic partial oxidation reactor 13 to the water-gas shift reactor 71. The oxidation product gas may be directed from the catalytic partial oxidation reactor 13 to the one or more third heat exchangers through lines 79 and 81, and the oxidation product gas may be directed to the reactor 89 through the lines 79 and 85. Flow to the first and second heat exchangers 11 and 17 may be precluded by closing valves 23 and 25.

As can be seen above, in certain embodiments of the process of the invention, certain steps of conditioning the oxidation product gas to be converted to methanol may be omitted. Therefore, in certain embodiments, a system for effecting the process of the invention need not include unnecessary elements.

In an embodiment, for example when the water-gas shifted oxidation product gas exiting the water-gas shift reactor 71 has a temperature within a selected range of temperatures for converting the water-gas shifted oxidation product gas to a methanol gas product in reactor 89, the step of cooling the water-gas shifted oxidation product gas in one or more third heat exchangers 59 need not be conducted. In this embodiment, the one or more third heat exchangers 59 may be excluded from the system for practicing the process of the invention, and the water-gas shifted oxidation product gas may be fed directly from the water-gas shift reactor 71 to the reactor 89 as a feedstock for conversion into a methanol gas product.

In an embodiment, for example, when 1) no additional hydrogen may be needed in the oxidation product gas and the step of contacting the oxidation product gas with a water-gas shift catalyst need not be conducted; and 2) when the oxidation product gas exiting the catalytic partial oxidation reactor or the cooled oxidation product exiting the first heat exchanger 11 and/or the one or more second heat exchangers 17 has a temperature within a selected range of temperatures for converting the oxidation product gas to a methanol product gas in reactor 89, the step of contacting the oxidation product gas with a water-gas shift catalyst need not be conducted and the step of cooling the oxidation product gas or the water-gas shifted oxidation product gas in one or more third heat exchangers 59 need not be conducted. In this embodiment, the water-gas shift reactor 71 and the one or more third heat exchangers 59 may be excluded from the system for practicing the process of the invention, and the oxidation product gas may be fed directly from the catalytic partial oxidation reactor 13 to the reactor 89 and/or the cooled oxidation product gas may be fed from the first heat exchanger 11 and/or the second heat exchanger 17 directly to the reactor 89.

At a temperature selected within the range of from 200° C. to 300° C. the oxidation product gas or the water-gas shifted oxidation product gas is reacted to form a methanol product gas. Methanol may be formed from the oxidation product gas or the water-gas shifted oxidation product gas according to the following reaction:

$$CO+2H_2 \leftrightarrows CH_3OH$$

where carbon dioxide may be involved mechanistically in the reaction, and increases the reaction rate. The quantity of carbon dioxide in the oxidation product gas or the water-gas shifted oxidation product gas is selected to be from 20 vol. % to 60 vol. %, or from 30 vol. % to 50 vol. %, or from 35 vol. % to 45 vol. % to optimize the rate that methanol may be formed from contact of catalyst with the oxidation product gas or the water-gas shifted oxidation product gas, where the quantity of carbon dioxide in the oxidation product gas may be selected by washing the extracted gas with a methanol wash as described above.

The oxidation product gas or the water-gas shifted oxidation product gas may be reacted to form a methanol product gas by contacting the oxidation product gas or water-gas shifted oxidation product gas with a selected methanation catalyst. The oxidation product gas or the water-gas shifted oxidation product gas may be contacted with the selected catalyst in a reactor 89, preferably by passing the oxidation product gas or water-gas shifted oxidation product gas over and/or through a fixed bed of the catalyst located in the reactor 89. The resulting methanol product gas may be comprised of a methanol gas, hydrogen, and carbon dioxide, where the methanol product gas typically may have a temperature of from 200° C. to 300° C. upon exiting the reactor 89.

The catalyst useful for catalyzing conversion of the oxidation product gas or water-gas shifted oxidation product gas to methanol may be selected from conventional commercially available catalysts for effecting conversion of a gas containing CO, $H_2$, and optionally $CO_2$, to methanol. Such catalysts may be formed of copper, zinc, and/or aluminum metals or their oxides. The amount of catalytically active metal in the catalyst may range from 2 wt. % to 75 wt. % of the catalyst, or from 3 wt. % to 40 wt. %, or from 5 wt. % to 25 wt. % of the catalyst. In an embodiment, a methanol catalyst may include from 0 to 20 wt. % Zn, from 40 to 50 wt. % Cu, and from 40 to 50 wt. % Al. In one embodiment, the methanol catalyst may be a copper-zinc-aluminum alloy. One such alloy may be formed of a $Cu/ZnO/Al_2O_3$ mixture.

The catalytically active metal may be supported on a porous carrier. The porous carrier may be selected from any of the suitable refractory metal oxides or silicates or combinations thereof known in the art. Particular examples of such porous carriers include silica, alumina, titania, zirconia, ceria, gallia, and mixtures thereof, preferably silica, alumina, and titania.

The resulting methanol product gas may optionally be passed from the reactor 89 to a hydrogen separator 111 via line 113. Hydrogen present in the methanol product gas may be separated in the hydrogen separator 111 and recycled back into the reactor 89 through line 115 or separated as a hydrogen gas product. It may be particularly useful to recycle hydrogen back into the reactor 89 as an excess of hydrogen facilitates the conversion of the oxidation product gas or the water-gas shifted oxidation product gas to the methanol product gas.

The hydrogen separator 111 preferably is effective at separating hydrogen as a low pressure gas from the methanol product gas while maintaining the methanol product gas at a higher pressure. For example, the hydrogen separated from the methanol product gas may have a pressure of from 0.1 MPa to 2 MPa, while the methanol product gas may have a pressure of from 5 MPa to 15 MPa.

Hydrogen separated by the hydrogen separator 111 that is to be recycled back into reactor 89 may need to be compressed to the pressure of the oxidation product gas or water-gas shifted oxidation product gas before being fed to the reactor 89. The separated hydrogen may be compressed by a compressor 117 to increase the pressure of the separated hydrogen prior to feeding the separated hydrogen back into the reactor 89. The separated hydrogen may be compressed to a pressure of from 5 MPa to 15 MPa. Energy ($e^-$) to drive the compressor 117 may be supplied from energy ($e^-$) produced by the expander 119, as described below.

In an embodiment, the hydrogen separator 111 comprises a hydrogen-permeable, hydrogen-selective membrane through which hydrogen—but no other components of the methanol product gas—may pass, and that is effective for operating at temperatures up to 400° C. Such a hydrogen-separation membrane may comprise a support coated with a thin layer of a metal or alloy that is selectively permeable to hydrogen. The support may be formed of a ceramic or metallic material that is porous to hydrogen. Porous stainless steel or porous alumina are preferred materials for the support of the membrane. The hydrogen selective metal or alloy coated on the support may be selected from metals from the group consisting of Pd, Pt, Ni, Ag, Ta, V, Y, Nb, Ce, In, Ho, La, Au, and Ru, and mixtures thereof, particularly in the form of alloys. Palladium and platinum alloys are preferred. A particularly preferred membrane useful in the present process has a very thin film of a palladium alloy having a high surface area coating a porous stainless steel support. Membranes of this type can be prepared using the methods disclosed in U.S. Pat. No. 6,152,987. Thin films of platinum or platinum alloys having a high surface area would also be suitable as the hydrogen selective material. The hydrogen-permeable, hydrogen-selective membrane may be in the form of a tube that the hydrocarbon oxygenate product gas or the hydrocarbon product gas may contact as either product gas passes through the hydrogen separator 111.

Alternatively, in an embodiment of the process, hydrogen is not separated by itself from the methanol product gas and no hydrogen separator 111 or compressor 117 is included in the system for practicing the process.

The methanol product gas, optionally less the hydrogen that had been present in the methanol product gas, may be passed to an expander 119 via line 121. The methanol product gas may be expanded through the expander 121 to depressurize the gas and to generate energy ($e^-$) as the gas is expanded through the expander 121. The expander 121 may be, for example, a turbine, where passage of the methanol product gas through the turbine generates electricity.

The energy ($e^-$) produced by expanding the methanol product gas through the expander 119 may be, and preferably is, sufficient to drive the unit 8 for separating oxygen from air, if utilized in the system for practicing the process, and to compress the hydrogen separated in the hydrogen separator 111 in compressor 117, again, if utilized in the system for practicing the process. The expander 119, therefore, may be operatively connected, e.g. by electrical connections, with the unit 8 for separating oxygen from air and/or with the compressor 117 for compressing hydrogen separated in the hydrogen separator 111. Optionally, any excess energy produced by expanding the methanol product gas through the expander 119 may be delivered for use outside the system for practicing the process of the present invention.

The expanded methanol product gas may then be condensed in condenser 123 at a temperature selected to be effective to separate a liquid methanol product from carbon dioxide and other gases in the methanol product gas that are not condensable at the selected temperature. The expanded methanol product gas may be provided to the condenser 123 from the expander via line 125.

The temperature selected to condense a liquid methanol product from an expanded methanol gas product should be in the range from above the sublimation point of carbon dioxide (−78° C.) to below the boiling point of methanol. In particular, the temperature for operating the condenser 123 to condense the liquid methanol product from the expanded methanol gas product should be selected within the range of above −78° C. to below 67° C., and preferably from 10° C. to 35° C.

The temperature at which the liquid methanol product may be condensed in the condenser 123 may be regulated with a coolant. The coolant may circulate through the condenser 123, for example through coolant coils or through a coolant jacket in the condenser, to exchange heat with the expanded methanol product gas and thereby condense the liquid methanol product from the gas. In a preferred embodiment, the coolant is water, and the water may be chilled water having a temperature of less than 25° C., or less than 20° C.

The liquid methanol product, which may optionally contain some water, may be separated as a product of the process from the condenser 123 through lines 127 and 131. The liquid methanol product may be utilized as described in more detail below. The process of the present invention is highly efficient, where at least 80%, or at least 85%, or at least 90%, on a molar basis, of carbon present in the hydrocarbons of the extracted gas may be recovered in the liquid methanol product.

In the process of the present invention the liquid methanol product separated from the methanol product gas is a first liquid methanol product. The first liquid methanol product may be separated into a methanol product portion and into a liquid methanol wash portion, where the methanol product portion may be removed from the processing system via line 131 for storage and transport or for further processing as described below. The liquid methanol wash portion may be directed to the scrubber 9 via lines 135 and 137 for use as a methanol wash utilized to scrub the extracted gas. A portion of the liquid methanol wash portion separated from the first liquid methanol product may be stored in a storage tank (not shown) for subsequent use as the methanol wash. The liquid methanol wash portion may be passed through a heat exchanger 139 to chill the liquid methanol wash portion to a temperature of from −40° C. to 0° C., or from −20° C. to −30° C. prior to injecting the liquid methanol wash portion into the scrubber 9 as the methanol wash to wash the extracted gas. Liquid nitrogen from the air separation unit 8 may be directed from the air separation unit 8 to the heat exchanger 139 via line 141 to cool the liquid methanol wash portion. The chilled liquid methanol wash portion may then be injected into the scrubber 9 to wash the extracted gas to produce the washed extracted gas and a carbon dioxide contaminated methanol wash product, where the carbon dioxide contaminated methanol wash product contains more carbon dioxide than the liquid methanol wash portion prior to washing the extracted gas in the scrubber 9.

A second liquid methanol product may be recovered from the carbon dioxide contaminated methanol wash product. In an embodiment of the process of the present invention, the carbon dioxide contaminated liquid methanol wash product may be removed from the scrubber via line 133 and fed into the condenser 123 prior to separating the second liquid methanol product from the carbon dioxide contaminated liquid methanol wash product. Liquid methanol may be separated from the carbon dioxide contaminated methanol wash product in the condenser 123 to form the second liquid methanol product, where the second liquid methanol product contains has a lower carbon dioxide content than the carbon dioxide contaminated methanol wash product. In this embodiment, the second liquid methanol product and the first liquid methanol product may be combined and collected from the condenser 123 as a combined liquid methanol product, and a portion of the combined liquid methanol product may be separated from the processing system as the methanol product portion via line 131 and a portion of the combined liquid methanol product may be separated and utilized as the liquid methanol wash portion which is fed to the scrubber 9 via lines 135 and 137 to wash the extracted gas.

Alternatively, a second liquid methanol product may be recovered from the carbon dioxide contaminated methanol wash product by feeding the carbon dioxide contaminated methanol wash product to a separate condenser (not shown), wherein the second liquid methanol product is separated from a carbon dioxide-rich gas. The second liquid methanol product contains less carbon dioxide than the carbon dioxide contaminated methanol wash product.

A carbon dioxide-rich gas may be separated from the condenser 123 through line 129. In an embodiment, the carbon dioxide-rich gas may be re-injected into the reservoir 1 through the well 3. Re-injection of the carbon dioxide rich gas into the reservoir 1 serves to reduce the amount of greenhouse gases emitted into the atmosphere as a result of conducting the process of the invention and also serves to maintain the reservoir pressure. In an embodiment, at least 85%, or at least 90%, or at least 95% of the carbon dioxide present in the extracted gas, on a mass basis, is recovered by separation from the condenser and is re-injected into the reservoir 1. Further, as described above, injection of carbon dioxide into the reservoir may serve to fracture the formation of the reservoir 1 to enable the production of further natural gas from the reservoir 1, particularly if the carbon dioxide is re-compressed prior to injecting it into the reservoir 1. In an embodiment, liquid nitrogen derived from separating the oxygen containing gas from air in the air separation unit 8 may be used to cool the carbon dioxide-rich gas, and the cooled carbon dioxide-rich gas may be compressed prior to injection to increase the efficiency of injection.

In an embodiment, the liquid methanol product may be transported and/or further processed. The liquid methanol product may be loaded into transport containers, for example liquid transport tanks, and then may be transported to a selected location. For example, liquid methanol product produced from a reservoir located offshore may be loaded into liquid transport tanks on a ship and then transported by the ship to a refinery for further processing.

The liquid methanol product that is methanol may be further processed to produce higher molecular weight hydrocarbon products either after being transported or at the well-site. In an embodiment of the process of the invention, the methanol recovered as liquid methanol product may be converted to a high octane gasoline product by the known methanol-to-gasoline process in which methanol may be converted to gasoline utilizing one or more catalysts such as solid acid catalysts including zeolite or silicaaluminophosphate molecular sieve catalysts. The liquid methanol product may be superheated and mixed with a synthesis gas, optionally the oxidation product gas, and contacted with a zeolite catalyst, in an embodiment a ZSM-5 zeolite, in a methanol conversion reactor (not shown) at a temperature of from 360° C. to 380° C. and a pressure of from 1.5 MPa to 2.5 MPa to produce a gasoline-containing product. Gasoline may be separated from the gasoline-containing product by distillation.

In another embodiment of the process of the invention, liquid methanol product may be converted to light olefins including ethene and propene according to known methanol-to-olefin processes. The liquid methanol product may be heated to a temperature of from 450° C. to 550° C. at a pressure of less than 1.5 MPa and contacted with a solid acid catalyst, such as a zeolite or a silicaaluminophosphate molecular sieve catalyst to produce the olefin product.

What is claimed is:

1. A process for recovering a natural gas contaminated with high levels of $CO_2$ and converting the natural gas into methanol, comprising:
   a) extracting a gas comprising carbon dioxide and methane from a reservoir containing natural gas, where carbon dioxide comprises greater than 40 vol. % of the extracted gas;
   b) scrubbing the extracted gas with a wash effective to produce a washed extracted gas containing less carbon dioxide than the extracted gas and to produce a carbon dioxide contaminated wash product, where the washed extracted gas contains at least 20 vol. % carbon dioxide and where the carbon dioxide contaminated wash product contains more carbon dioxide than the wash;
   c) oxidizing the washed extracted gas with an oxygen containing gas in the presence of a partial oxidation catalyst at a temperature of 900° C. or less to produce an oxidation product gas containing hydrogen, carbon monoxide, and carbon dioxide, where the molar ratio of oxygen from the oxygen containing gas to carbon from the hydrocarbons in the extracted gas is less than one;
   d) optionally contacting the oxidation product gas with steam and a water-gas shift catalyst at a temperature of from 200° C. to 400° C. and a pressure of from 0.1 MPa to 15 MPa to produce a water-gas shifted oxidation product gas;
   e) contacting the oxidation product gas or the water-gas shifted oxidation product gas with a methanol synthesis catalyst at a temperature of from 200° C. to 300° C. and a pressure of from 5 MPa to 15 MPa to produce a methanol product gas comprising methanol and carbon dioxide; and
   f) separating a first liquid methanol product from the methanol product gas.

2. The process of claim 1 wherein the wash used to scrub the extracted gas is comprised of liquid methanol.

3. The process of claim 1 further comprising the steps of:
   a) separating a portion of the first liquid methanol product;
   b) optionally storing the separated portion of the first liquid methanol product;
   c) chilling the separated portion of the first liquid methanol product to a temperature of from −40° C. to 0° C.;
   d) scrubbing the extracted gas with the separated chilled portion of the first liquid methanol product to form the washed extracted gas and a carbon dioxide contaminated liquid methanol wash product.

4. The process of claim 2 further comprising the step of separating a second liquid methanol product from the carbon dioxide contaminated methanol wash product wherein the second liquid methanol product contains less carbon dioxide than the carbon dioxide contaminated methanol wash product.

5. The process of claim 3 wherein the carbon dioxide contaminated methanol wash product is combined with the methanol product gas prior to separating the second liquid methanol product from the carbon dioxide contaminated methanol wash, where the first liquid methanol product from the methanol product gas and the second liquid methanol product from the carbon dioxide contaminated methanol wash product are separated together from the methanol product gas and the carbon dioxide contaminated methanol wash product, respectively, as a combined liquid methanol product.

6. The process of claim 5 wherein the step of separating a portion of the first liquid methanol product comprises separating a portion of the combined liquid methanol product; the step of optionally storing the separated portion of the first liquid methanol product comprises optionally storing the separated portion of the combined liquid methanol product; the step of chilling the separated portion of the first liquid methanol product comprises chilling the separated portion of the combined liquid methanol product; and the step of utilizing the separated chilled portion of the first liquid methanol product as the methanol wash to wash the extracted gas comprises utilizing the separated chilled portion of the combined liquid methanol product as the methanol wash to wash the extracted gas.

7. The process of claim 5 wherein the wash used to scrub the extracted gas is comprised of an amine.

8. The process of claim 1 wherein the extracted gas is scrubbed with an amount of wash effective to produce a washed extracted gas containing from 20 vol. % to 60 vol. % carbon dioxide.

9. The process of claim 1 wherein the washed extracted gas is oxidized with the oxygen containing gas in the presence of the partial oxidation catalyst at a temperature of 800° C. or less.

10. The process of claim 1 wherein carbon dioxide comprises more than 60 vol. % of the extracted gas.

11. The process of claim 1 further comprising recovering at least 80%, on a molar basis, of carbon initially present in the hydrocarbons of the extracted gas in the first liquid methanol product.

12. The process of claim 1 further comprising the step of separating hydrogen from the methanol product gas prior to separating the first liquid methanol product from the methanol product gas.

13. The method of claim 12 further comprising the steps of:
   a) compressing the separated hydrogen to a pressure of from 5 MPa to 15 MPa; and
   b) mixing the compressed separated hydrogen with the oxidation product gas or the water-gas shifted oxidation product gas prior to contacting the oxidation product gas or the water-gas shifted oxidation product gas with the methanol synthesis catalyst to produce the methanol product gas.

14. The process of claim 1 wherein the partial oxidation catalyst comprises rhodium and iridium.

15. The process of claim 1 wherein the oxygen containing gas contains at least 90 vol. % oxygen.

16. The process of claim 1 wherein the washed extracted gas is oxidized with the oxygen containing gas in the presence of steam.

17. The process of claim 16 further comprising mixing steam with the washed extracted gas and the oxygen containing gas prior to oxidizing the washed extracted gas, wherein the amount of steam mixed with the washed extracted gas and the oxygen containing gas is selected to provide a molar ratio of steam to carbon from hydrocarbons in the washed extracted gas of greater than 0 and less than 0.4.

* * * * *